US012589216B2

(12) United States Patent (10) Patent No.: US 12,589,216 B2
Sun et al. (45) Date of Patent: Mar. 31, 2026

(54) SEALING VALVE AND CLOSED STRUCTURE ANESTHETIC BOTTLE

(71) Applicants: LINKR MEDICAL (SHANGHAI) CO., LTD., Shanghai (CN); SHENZHEN COLINN MEDICAL CO., LTD., Guangdong (CN)

(72) Inventors: Xiangming Sun, Shanghai (CN); Yushun Wang, Shanghai (CN); Gang Shen, Shanghai (CN)

(73) Assignees: LINKR MEDICAL (SHANGHAI) CO., LTD., Shanghai (CN); SHENZHEN COLINN MEDICAL CO., LTD., Shenzhen (CN)

( * ) Notice: Subject to any disclaimer, the term of this patent is extended or adjusted under 35 U.S.C. 154(b) by 285 days.

(21) Appl. No.: 17/781,981

(22) PCT Filed: Apr. 13, 2021

(86) PCT No.: PCT/CN2021/086885
§ 371 (c)(1),
(2) Date: Oct. 20, 2022

(87) PCT Pub. No.: WO2022/217452
PCT Pub. Date: Oct. 20, 2022

(65) Prior Publication Data
US 2024/0157084 A1     May 16, 2024

(51) Int. Cl.
*A61M 16/18*     (2006.01)
*A61J 1/20*     (2006.01)
*A61M 16/20*     (2006.01)

(52) U.S. Cl.
CPC ............ *A61M 16/18* (2013.01); *A61J 1/2037* (2015.05); *A61J 1/2051* (2015.05); *A61J 1/2089* (2013.01);
(Continued)

(58) Field of Classification Search
CPC ................ A61M 16/20; A61M 16/183; A61M 2202/0241; A61M 2205/0238;
(Continued)

(56) References Cited

U.S. PATENT DOCUMENTS 5,505,236 A     4/1996  Grabenkort et al.
8,500,088 B2 *  8/2013  Freed .................. A61M 16/183
                                                        251/149.3
(Continued)

FOREIGN PATENT DOCUMENTS

CN        2841000 Y    11/2006
CN     201700632 U     1/2011
(Continued)

OTHER PUBLICATIONS

International Search Report for International Application No. PCT/CN2021/086885; Date of Completion: Dec. 24, 2021; Date of Mailing: Jan. 14, 2022; 5 Pages.
(Continued)

*Primary Examiner* — Marina A Tietjen
(74) *Attorney, Agent, or Firm* — CANTOR COLBURN LLP

(57) ABSTRACT

The present application discloses a sealing valve (10), including a guiding tube (1), comprising a first end (11) configured to be inserted into an outer packaging bottle and a second end configured to be connected to an anesthesia vaporizer (12); the outer peripheral surface of the first end (11) is provided with a convex ring (111) protruding toward the inner wall of the outer packaging bottle and abutting against the inner wall of the outer packaging bottle; and a pushing rod (2) configured to be arranged in the guiding tube (1) and slidable along an axial direction of the guiding tube (1) to connect the anesthesia vaporizer with the outer packaging bottle or to block between the anesthesia vaporizer and the outer packaging bottle.

20 Claims, 6 Drawing Sheets

(52) U.S. Cl.
CPC .......... *A61M 16/183* (2013.01); *A61M 16/20* (2013.01); *A61M 2202/0241* (2013.01); *A61M 2205/0238* (2013.01); *A61M 2205/584* (2013.01); *A61M 2205/586* (2013.01)

(58) Field of Classification Search
CPC ........ A61M 2205/584; A61M 2205/586; A61J 1/2037; A61J 1/2051; A61J 1/2089
See application file for complete search history.

(56) References Cited

U.S. PATENT DOCUMENTS

| | | | |
|---|---|---|---|
| 10,625,041 B2 | 4/2020 | Sun et al. | |
| 2019/0083737 A1* | 3/2019 | Sun ..................... | A61M 16/183 |

FOREIGN PATENT DOCUMENTS

| | | |
|---|---|---|
| CN | 104595541 A | 5/2015 |
| CN | 109562021 A | 4/2019 |
| CN | 211392279 U | 9/2020 |
| JP | 2004106852 A | 4/2004 |
| WO | 2010104756 A1 | 9/2010 |
| WO | 2015034978 A1 | 3/2015 |
| WO | 2016203208 A1 | 12/2016 |

OTHER PUBLICATIONS

Written Opinion for International Application No. PCT/CN2021/086885; Date of Completion: Jan. 10, 2022; Date of Mailing: Jan. 14, 2022; 4 Pages.

* cited by examiner

40

404

1121

1

SEALING VALVE AND CLOSED STRUCTURE ANESTHETIC BOTTLE

CROSS REFERENCE TO RELATED APPLICATIONS

This application is a National Stage of PCT Application No. PCT/CN2021/086885 filed on Apr. 13, 2021, the contents of which are incorporated herein by reference thereto.

BACKGROUND

Technical Field

The application relates to the technical field of anesthetics filling system, in particular to a sealing valve and a closed structure anesthetic bottle.

Description of Related Art

The general outer packaging, even if fully closed during storage and transportation, cannot guarantee the complete sealing during and after unpacking. For inhaled anesthetics such as sevoflurane, isoflurane, and desflurane, it is necessary to unpack and transfer the drug to the anesthesia vaporizer in use. The traditional solution is to unpack the outer packaging bottle first, and then add the drug in the outer packaging bottle into the anesthesia vaporizer through a dosing port or install an adapter on the outer packaging bottle containing the drug, and add the drug to the anesthesia vaporizer through the adapter. Due to the volatile physical properties of the inhaled anesthetic and the special use scene and function, if the sealing property during the operation mentioned above cannot be guaranteed, the inhaled anesthetic will easily volatilize to the air environment during use, which will pollute the operating room environment, and is not conducive to the health of medical staff, and threaten the safety of the entire operation.

Generally, a sealing ring is provided at the connection between the mouth of the outer packaging bottle and the adapter, the liquid and gas in the outer packaging bottle will overflow to and contact with the sealing ring, which will affect the purity of the drug.

SUMMARY

The purpose of the embodiments of this application is to provide a sealing valve and a closed anesthetic bottle, comprising but not limited to solving the problem in the prior art: liquid and gas in the outer packaging bottle overflowing to and contacting the sealing ring between the bottle mouth and the sealing valve, which will affect the purity of the drug.

The technical solutions adopted in the embodiments of this application are: In a first aspect, a sealing valve is provided, comprising: a guiding tube, configured for guiding an anesthetic from an outer packaging bottle to an anesthesia vaporizer, and comprising a first end configured to be inserted into the outer packaging bottle and a second end configured to be connected to the anesthesia vaporizer; a convex ring, provided at an outer peripheral surface of the first end, protruding toward an inner wall of the outer packaging bottle and abutting against the inner wall of the outer packaging bottle; and a pushing rod, arranged in the guiding tube and slidable along an axial direction of the guiding tube to enable the guiding tube to connect the anesthesia vaporizer with the outer packaging bottle or to block between the anesthesia vaporizer and the outer packaging bottle.

In one embodiment, the inner tube wall of the guiding tube is provided with an annular protrusion which is arranged around the axis of the guiding tube, and one end of the pushing rod close to the second end abuts against the annular protrusion.

In one embodiment, the sealing valve further includes a first spring and a clamping block arranged in the guiding tube, and the clamping block is fixed to one end of the guiding tube close to the first end. One end of the pushing rod close to the second end is provided with a flange, and the spring is sleeved outside of the pushing rod, and both ends of the first spring abut against the flange and the clamping block, respectively.

In one embodiment, the sealing valve further includes a blocking member for blocking the first end of the guiding tube and capable of moving and opening the first end of the guiding tube under the pushing of the pushing rod.

In one embodiment, a surface of the blocking member facing the pushing rod is provided with a positioning groove, configured for positioning the pushing rod when the pushing rod pushes the blocking member.

In one embodiment, the sealing valve further includes a second spring arranged in the guiding tube, configured for driving the blocking member to move to the first end to block the first end.

In one embodiment, the sealing valve further includes a bracket fixed to the guiding tube, the bracket is configured to be arranged in the outer packaging bottle, the bracket is fixed to the first end, and has an opening cavity and a perfusion port communicating with the opening cavity; the blocking member and the second spring are both located in the opening cavity; both ends of the second spring abut against the blocking member and the bracket.

In one embodiment, the sealing valve further includes a first sealing member located between the blocking member and the first end and sealing the gap therebetween.

In one embodiment, the end of the pushing rod close to the second end is provided with a positioning structure for positioning the anesthesia vaporizer for docking when the anesthesia vaporizer is inserted into the guiding tube.

In one embodiment, the convex ring is a plastic convex ring, and the plastic convex ring and the guiding tube are integrally formed.

In a second aspect, a closed anesthetic bottle is provided, comprising a bottle body and the aforementioned sealing valve, and the convex ring abuts against the inner wall of the opening of the bottle body.

In one embodiment, one end of the guiding tube close to the first end is provided with a first connecting portion in a ring shape, and the first connecting portion is located outside the bottle body and fixed to the opening of the bottle body.

In one embodiment, a second sealing gasket is provided between the first connecting portion and the opening of the bottle body, and the first connecting portion includes: an annular convex disk integrally connected to the guiding tube, and the annular convex disk protrudes radially outward along the guiding tube and is arranged around the outer tube wall of the first end, and the annular convex disk is fixed at the opening of the bottle body; sealing convex portion arranged on the side of the annular convex disk facing the sealing gasket, and the sealing convex portion surrounds the guiding tube and extends in the circumferential direction of the guiding tube and abuts against the second sealing gasket.

In one embodiment, the closed anesthetic bottle further includes a ring cap, which is sheathed at the first connecting portion and the opening of the bottle body.

In one embodiment, the closed anesthetic bottle further includes a bottle cap sleeved on the outer tube wall of the sealing valve, the bottle cap includes a top end and an open end, and the first end of the guiding tube is provided with a second connecting portion, the top end is provided with a third connecting portion that cooperates with the second connecting portion.

In one embodiment, the top end is provided with a sealing tube portion, and the sealing tube portion and the third connecting portion clamp the second connecting portion and hermetically cooperate with the second connecting portion.

In one embodiment, the first end of the guiding tube is further provided with a sealing ring, an annular pressure-stabilizing groove is formed between the sealing ring and the second connecting portion, and the sealing tube portion is inserted into the annular pressure-stabilizing groove and hermetically cooperates with the second connecting portion and the sealing ring.

In one embodiment, the second connecting portion is formed by protruding inward from the outer surface of the top end.

In one embodiment, the second connecting portion is provided with an slot on a side close to the outer surface of the top end.

In one embodiment, the outer circumference of the ring wall of the bottle cap is provided with a plurality of ridges.

The beneficial effect of the sealing valve provided by the embodiments of the present application is that the outer peripheral surface of the first end is provided with a convex ring protruding toward the inner wall of the outer packaging bottle and abutting against the inner wall of the outer packaging bottle, so that there will be no liquid or gas overflow between the inner wall of the outer packaging bottle and the outer wall of the first end; when a sealing ring is set when the sealing valve is connected to the mouth of the outer packaging bottle, it can prevent the gas or liquid in the outer packaging bottle from overflowing and contacting the sealing ring, so that the purity of the liquid drug in the outer packaging bottle can be ensured, and the sealing property of the outer packaging bottle can be improved at the same time; the gas pressure in the outer packaging bottle will expand the convex ring, further improving the sealing property of the connection between the convex ring and the mouth of the outer packaging bottle.

The beneficial effect of the closed anesthetic bottle provided by the embodiment of the present application is that since the convex ring abuts against the inner wall of the opening of the bottle, there is no liquid or gas overflow between the inner wall of the bottle and the outer wall of the first end; when the sealing ring is set when the sealing valve is connected to the mouth of the bottle, it can prevent the gas or liquid in the bottle from overflowing and contacting the sealing ring, so as to ensure the purity of the liquid drug in the bottle and improve the sealing property of the outer packaging bottle; the gas pressure in the bottle body will expand the convex ring, further improving the sealing property of the connection between the convex ring and the inner wall of the mouth of the bottle body.

BRIEF DESCRIPTION OF THE DRAWINGS

In order to more clearly describe the technical solutions in the embodiments of the present application, the following will briefly introduce the accompanying drawings that need to be used in the description of the embodiments or exemplary technologies. Obviously, the accompanying drawings in the following description are only of the present application. Those skilled in the art can obtain other drawings based on these drawings without creative work.

The reference signs in the Figure.

Figure 1:
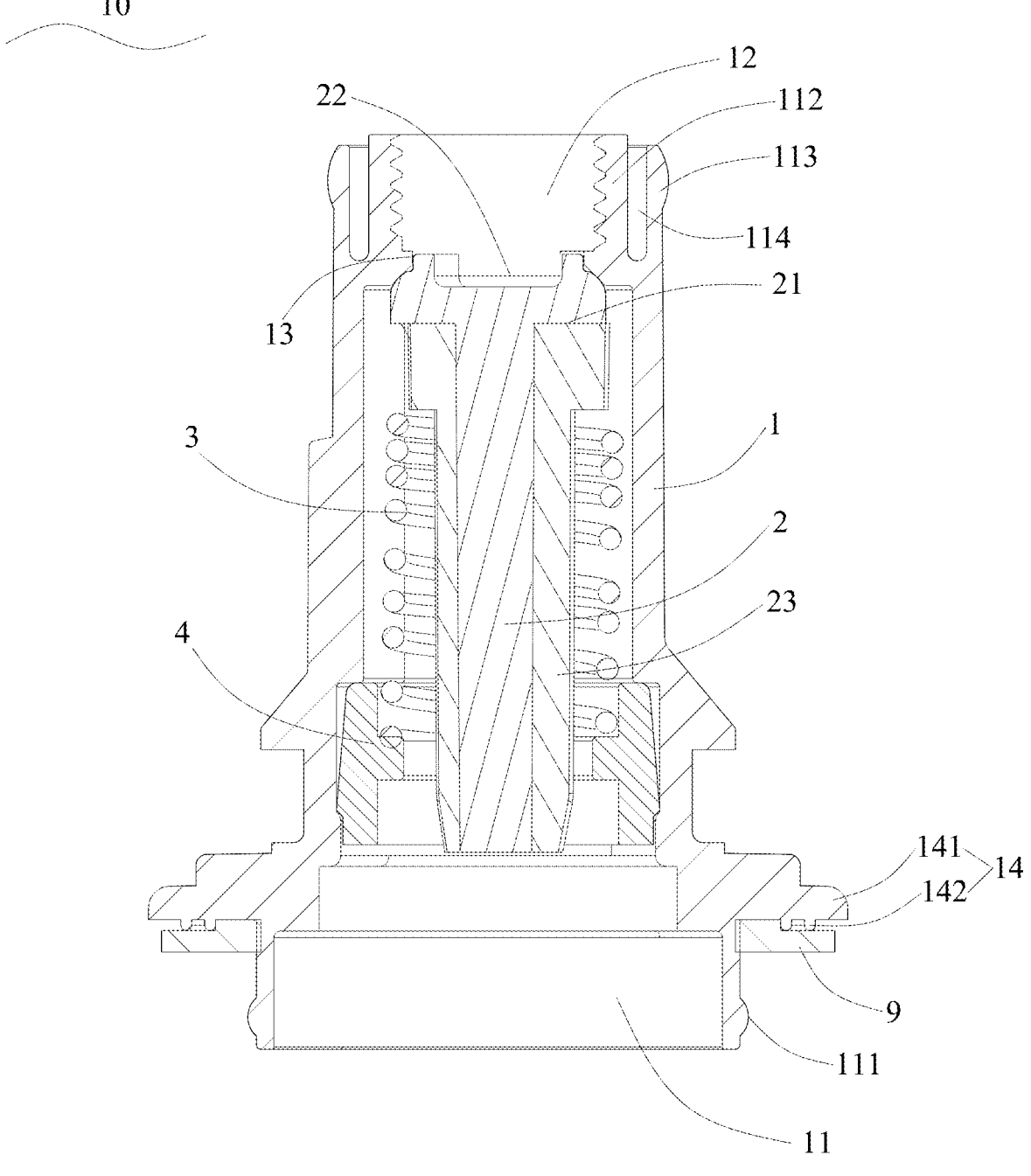
FIG. 1 is a schematic structural diagram of a first embodiment of a sealing valve provided by an embodiment of the present application.

10—sealing valve; 1—guiding tube; 11—first end; 111—convex ring; 112—second connecting portion; 1121—slot; 113—sealing ring; 114—pressure-stabilizing groove; 12—second end; 13—annular protrusion; 14—first connecting portion; 141—annular convex disc; 142—sealing convex portion; 2—pushing rod; 21—flange; 22—positioning structure; 23—flow guide plate; 3—first spring; 4—clamping block; 5—blocking element; 51—positioning groove; 6—second spring; 7—bracket; 72—perfusion port; 8—first sealing member; 20—bottle body; 201—opening; 9—second sealing gasket; 30—ring cap; 40—bottle cap; 401—top end; 4011—third connecting portion; 4012—sealing tube portion; 4013—limiting step; 402—open end; 404—ridges.

DETAILED DESCRIPTION OF THE
EMBODIMENTS

In order to make the purpose, technical solutions, and advantages of this application clearer, the following further describes the application in detail with reference to the accompanying drawings and embodiments. It should be understood that the specific embodiments described here are only used to explain the present invention, and are not used to limit the application.

It should be noted that when a component is referred to as being "fixed to" or "installed on" another component, it can be directly or indirectly on the other component. When a component is said to be "connected" to another component, it can be directly or indirectly connected to the other component. The terms "upper", "lower", "left", "right", etc. indicate the orientation or positional relationship based on the orientation or positional relationship shown in the drawings, and are only for ease of description, and do not indicate or imply the device or the element referred to must have a specific orientation, be constructed and operated in a specific orientation, and therefore cannot be construed as a limitation of the application. For those skilled in the art, the specific meaning of the above terms can be understood according to specific conditions. The terms "first" and "second" are only used for ease of description, and cannot be understood as indicating or implying relative importance or implicitly indicating the number of technical features. The meaning of "plurality" means two or more than two, unless otherwise specifically defined.

In order to illustrate the technical solutions provided by the present application, detailed descriptions are given below in conjunction with specific drawings and embodiments.

Figure 2:
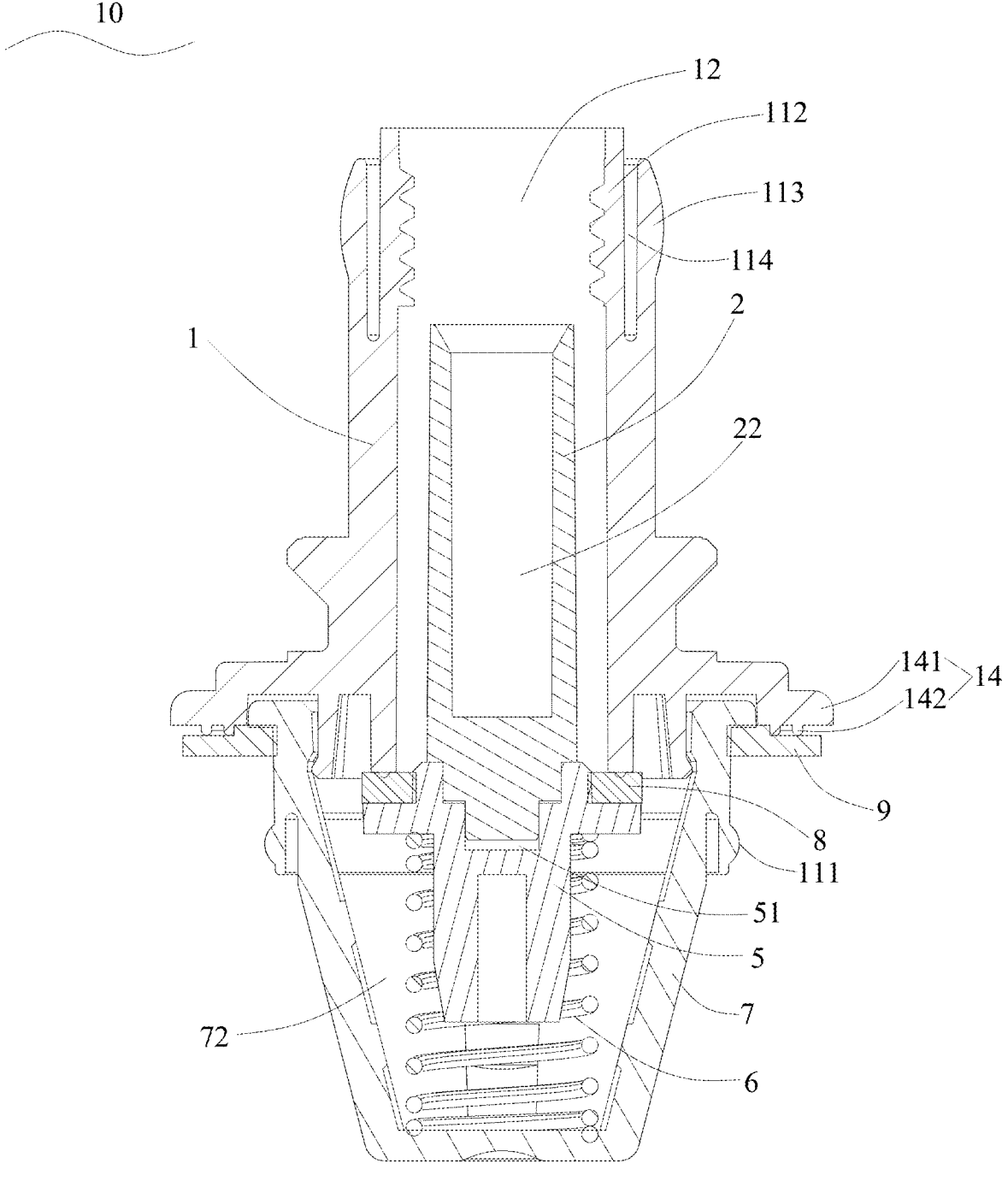
FIG. 2 is a schematic structural diagram of a second embodiment of the sealing valve provided by the embodiment of the present application.

Referring to FIGS. 1 and 2, some embodiments of the present application provide a sealing valve 10. The sealing valve 10 includes a guiding tube 1 for guiding an anesthetic from the outer packaging bottle to an anesthesia vaporizer, and the guiding tube 1 includes a first end 11 inserted into the outer packaging bottle and a second end 12 connected to the anesthesia vaporizer; the outer peripheral surface of the first end 11 is provided with a convex ring 111 protruding toward the inner wall of the outer packaging bottle and abutting against the inner wall of the outer packaging bottle; and a pushing rod 2 arranged in the guiding tube 1, the pushing rod 2 can slide along the axial direction of the guiding tube 1 to conduct the guiding tube 1 and block the anesthesia vaporizer and the outer packaging bottle. It should be noted that the sealing valve 10 is mainly used for delivering desflurane which is one of the anesthetics with a boiling point of 22.8° C. which is close to room temperature, so part of the desflurane will be gaseous at room temperature. Therefore, it needs to be installed in a dedicated anesthetic vaporizer. When in use, the first end 11 of the guiding tube 1 is inserted into the outer packaging bottle, and when the anesthetic in the outer packaging bottle needs to be guided to the anesthesia vaporizer, the drug feeding tube of the anesthesia vaporizer is inserted into the second end 12 of the guiding tube 1 of the sealing valve 10; when the drug feeding tube of the anesthesia vaporizer is inserted into the second end 12, the pushing rod 2 located in the guiding tube 1 is pushed toward the first end 11 along the axial direction of the guiding tube 1, so that the guiding tube 1 conducts the anesthesia vaporizer and the outer packaging bottle, and the anesthetic in the outer packaging bottle is guided to the anesthesia vaporizer through the guiding tube 1.

Compared with the prior art, the sealing valve 10 provided by the present application is provided with a convex ring 111 protruding toward the inner wall of the outer packaging bottle and abutting against the inner wall of the outer packaging bottle on the outer peripheral surface of the first end 11, thus, there will be no liquid or gas overflow between the inner wall of the outer packaging bottle and the outer wall of the first end 11. When the sealing valve 10 is connected to the mouth of the outer packaging bottle, the gas or liquid in the outer packaging bottle can be prevented from overflowing and contacting with the sealing ring, so as to ensure the purity of the liquid drug in the outer packaging bottle, and at the same time improve the sealing property of the outer packaging bottle; the gas pressure in the outer packaging bottle will expand the convex ring 111 to further improve the sealing property of the connection between the ring 111 and the inner wall of the mouth of the outer packaging bottle.

In some embodiments of the present application, referring to FIG. 1, the inner tube wall of the guiding tube 1 is provided with an annular protrusion 13 arranged around the axis of the guiding tube 1, and one end of the pushing rod 2 close to the second end 12 abuts against the annular protrusion 13. Since the end of the pushing rod 2 close to the second end 12 abuts against the annular protrusion 13, the second end 12 of the guiding tube 1 can be pushed by the pushing rod 2 to block the anesthetic vaporizer and the outer packaging bottle, preventing the anesthetic from passing through the second end 12 of the guide tube 1, and the annular protrusion 13 also prevents the pushing rod 2 from falling out of the guiding tube 1 from the second end 12, thereby improving the sealing property of the sealing valve 10 during transportation and storage. When it is necessary to introduce the anesthetic in the outer packaging bottle to the anesthesia vaporizer, the drug feeding tube of the anesthesia vaporizer is inserted into the guiding tube 1 to push the pushing rod 2 to move toward the first end 11, so that the annular protrusion 13 and the pushing rod 2 is separated, and the guiding tube 1 conducts the anesthesia vaporizer and the outer packaging bottle, and the anesthetic in the outer packaging bottle can be guided into the anesthesia vaporizer through the guiding tube 1.

In some embodiments of the present application, the sealing valve 10 further includes a first spring 3 and a clamping block 4 arranged in the guiding tube 1. The clamping block 4 is fixed in one end of the guiding tube 1 close to the first end 11 and the pushing rod 2 is provided with a flange 21 at one end close to the second end 12, the first spring 3 is sleeved outside of the pushing rod 2, and both ends of the first spring 3 abut against the flange 21 and the clamping block 4 respectively. The clamping block 4 is fixed to one end of the guiding tube 1 close to the first end 11 in a manner of fasteners or clamping, as long as the clamping block 4 can be relatively fixed to the guiding tube 1. Those skilled in the art can choose settings according to actual needs. During the transportation of the sealing valve 10, since the two ends of the first spring 3 abut against the flange 21 of the pushing rod 2 and the clamping block 4 respectively, the clamping block 4 is fixed in one end of the guiding tube 1 close to the first end 11, and under the elastic restoring force of the first spring 3, the flange 21 of the pushing rod 2 drives the flange 21 to move to the second end 12, so that the end of the pushing rod 2 close to the second end 12 can keep abutting against the annular protrusion 13, which enables the guiding tube 1 to block the anesthesia vaporizer and the outer packaging bottle, and improves the sealing property of the sealing valve 10 during transportation and storage. In a specific implementation, the side wall of the pushing rod 2 can be connected to at least two flow guide plates 23 which are evenly arranged on the peripheral side of the pushing rod and both extend along the length direction of the pushing rod 2, and the first spring 3 is sleeved outside of the flow guide plate 23, the flange 21 can also be provided on the flow guide plate 23; any two adjacent flow guide plates 23, the side wall of the pushing rod 2 between the two flow guide plates 23, and the tube wall of flow guide plate between the two flow guide plates 23 together forms a flow guide cavity for the passage of the anesthetic. In this way, the contact area between the pushing rod 2 and the tube wall of the guiding tube 1 can be reduced, and the wear of the lumen of the guiding tube 1 and the pushing rod 2 can be reduced. When it is necessary to introduce the anesthetic in the outer packaging bottle to the anesthesia vaporizer, the drug feeding tube of the anesthesia vaporizer is inserted into the guiding tube 1, and the pushing rod 2 located in the guiding tube 1 is pushed toward the first end 11 along the axis of the guiding tube 1, so that the end of the pushing rod 2 close to the second end 12 leaves the annular protrusion 13, and the guiding tube 1 conducts the anesthesia vaporizer and the outer packaging bottle, and the anesthetic in the outer packaging bottle is guided into the anesthesia vaporizer through the guiding tube 1.

In some embodiments of the present application, referring to FIG. 2, the sealing valve 10 further includes a blocking member 5 which is used to block the first end 11 of the guiding tube 1, and can be pushed by the pushing rod 2 to move and open the first end 11 of the guiding tube 1. Since the blocking member 5 blocks the first end 11 of the guiding tube 1, the first end 11 of the guiding tube 1 can block the anesthesia vaporizer and the outer packaging bottle, which prevents the anesthetic passing through the first end 11 of the guiding tube 1, then flowing through the second end 12, and then flowing into the air to pollute the environment, thereby improving the sealing property of the sealing valve 10 during transportation and storage. When it is necessary to introduce the anesthetic in the outer packaging bottle to the anesthesia vaporizer, the drug feeding tube of the anesthesia vaporizer is inserted into the guiding tube 1 to push the pushing rod 2 to move toward the first end 11, so that the blocking member 5 is away from the first end 11, enabling the guiding tube 1 to conduct the anesthesia vaporizer and the outer packaging bottle, and the anesthetic in the outer packaging bottle can be guided into the anesthesia vaporizer through the guiding tube 1.

In some embodiments of the present application, the surface of the blocking member 5 facing the pushing rod 2 is provided with a positioning groove 51 for positioning the pushing rod 2 when the pushing rod 2 pushes the blocking member 5. The positioning groove 51 is arranged so that the pushing rod 2 can be inserted into the positioning groove 51 of the blocking member 5 simply and conveniently, and then the blocking member 5 can be pushed.

In some embodiments of the present application, the sealing valve 10 further includes a second spring 6 arranged in the guiding tube 1 for driving the blocking member 5 to move to the first end 11 and block the first end 11. The arrangement of the second spring 6 is more conducive to the sealing of the first end 11 by the sealing member 5, and improves the sealing property of the sealing valve 10 during transportation and storage.

In some embodiments of the present application, the sealing valve 10 further includes a bracket 7 fixed to the guiding tube 1. The bracket 7 is arranged in the outer packaging bottle, and fixed to the first end 11, and the bracket 7 has an open mouth (not shown) and a perfusion port 72 communicating with the opening cavity; the blocking member 5 and the second spring 6 are both located in the opening cavity; the two ends of the second spring 6 abut against the blocking member 5 and the bracket 7 respectively. In a specific implementation, the first end 11 may be located in the opening cavity, and the first end 11 may also be located outside the opening cavity; when the first end 11 is provided in the opening cavity, the convex ring 111 is provided on the outer wall of the bracket 7; when the first end 11 is provided outside the opening cavity, the convex ring 111 is provided on the outer peripheral surface of the first end 11, and those skilled in the art can choose settings according to actual needs. During the transportation of the sealing valve 10, since the bracket 7 is fixed to the first end 11, the blocking member 5 and the second spring 6 are both located in the opening cavity of the bracket 7, and the two ends of the second spring 6 abut against the blocking member 5 and the bracket 7 respectively, and the second spring 6 drives the blocking member 5 to move to the first end 11 under the elastic restoring force to block the first end 11, so that the guiding tube 1 blocks the anesthesia vaporizer and the outer packaging bottle, improving the sealing property of the sealing valve 10 during transportation and storage. When it is necessary to introduce the anesthetic in the outer packaging bottle to the anesthesia vaporizer, the drug feeding tube of the anesthesia vaporizer is inserted into the guiding tube 1, and the pushing rod 2 located in the guiding tube 1 is pushed toward the first end 11 along the axis of the guiding tube 1, so that the pushing rod 2 pushes the blocking member 5 to move and open the first end 11 of the guiding tube 1, and the guiding tube 1 conducts the anesthesia vaporizer and the outer packaging bottle, and the anesthetic in the outer packaging bottle is guided into the anesthesia vaporizer through the perfusion port 72 of the bracket 7 and the guiding tube 1 sequentially.

In some embodiments of the present application, the sealing valve 10 further includes a first sealing member 8 located between the blocking member 5 and the first end 11 and sealing the gap therebetween. In this way, the sealing property of the first end 11 is further improved.

In some embodiments of the present application, referring to FIGS. 1 and 2, one end of the pushing rod 2 close to the second end 12 is provided with a positioning structure 22 for positioning the anesthesia vaporizer when the anesthesia vaporizer is inserted into the guiding tube 1, which is convenient for docking. The positioning structure 22 provided at one end of the pushing rod 2220 close to the second end 12 and matched with the drug feeding tube of the anesthesia vaporizer provides guide when the drug feeding tube of the anesthesia vaporizer is inserted into the guiding tube 1, which can easily and conveniently insert the drug feeding tube of the anesthesia vaporizer into the guiding tube 1 to prevent misoperation and avoid the volatilization and overflow of drugs from the sealing valve 10 when the drug feeding tube of the anesthesia vaporizer is inserted. In a specific implementation, the positioning structure 22 may be a recess corresponding to the nozzle structure of the drug feeding tube of the anesthesia vaporizer. A corresponding protrusion structure is provided at the mouth of the drug feeding tube of the anesthesia vaporizer. The positioning structure 22 is aligned with the central axis of the guiding tube 1 and inserted into the guiding tube 1. The positioning structure 22 has a simple structure, which is convenient for processing and can effectively position and insert the drug feeding tube of the anesthesia vaporizer with the central axis of the guiding tube 1.

In some embodiments of the present application, the convex ring 111 is a plastic convex ring 111, and the plastic convex ring 111 and the guiding tube 1 are integrally formed. The plastic convex ring 111 can withstand contents with a variety of different chemical properties, and has the characteristics of self-lubrication, wear resistance and good toughness, so that the convex ring 111 can maintain a reliable contact with the inner wall of the outer packaging bottle and the convex ring 111 can be more smoothly inserted into the inner wall of the outer packaging bottle.

Figure 3:
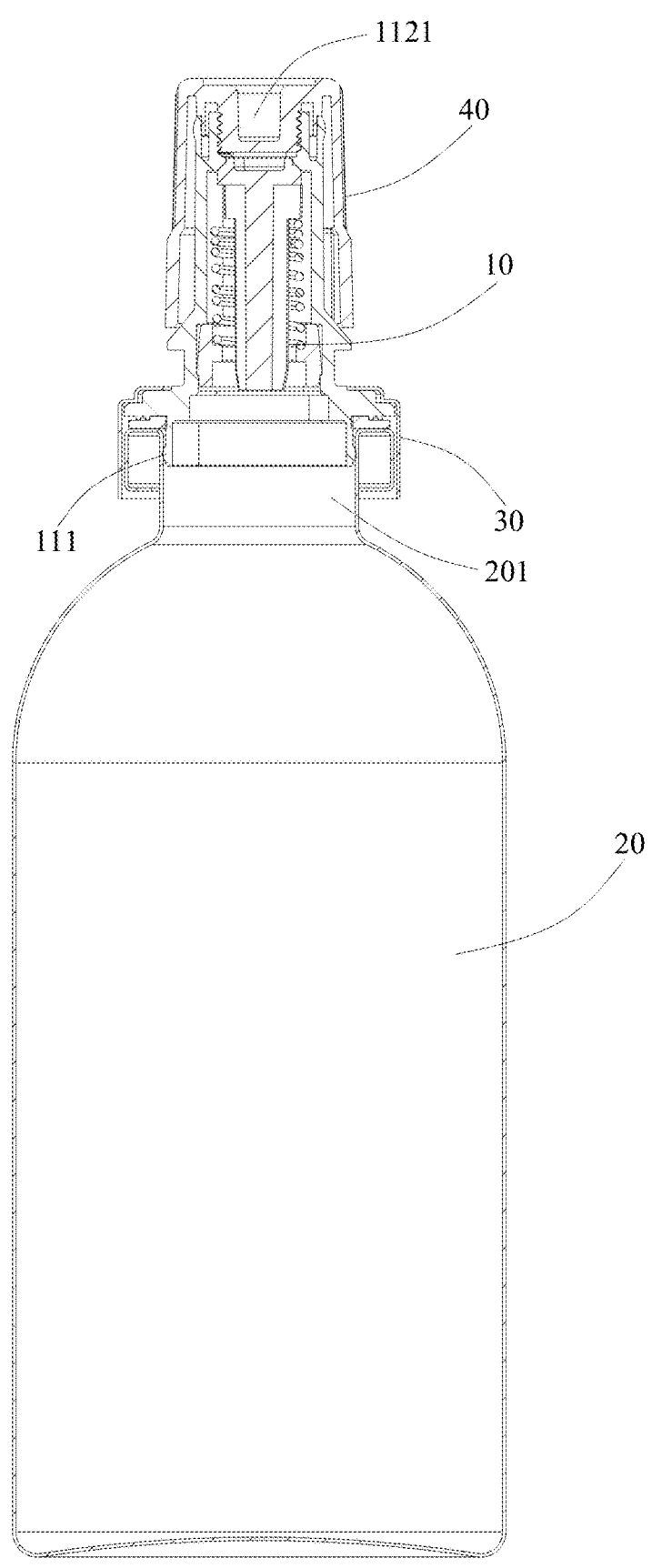
FIG. 3 is a schematic structural diagram of a closed anesthetic bottle comprising the sealing valve in FIG. 1 provided by an embodiment of the present application.
Figure 4:
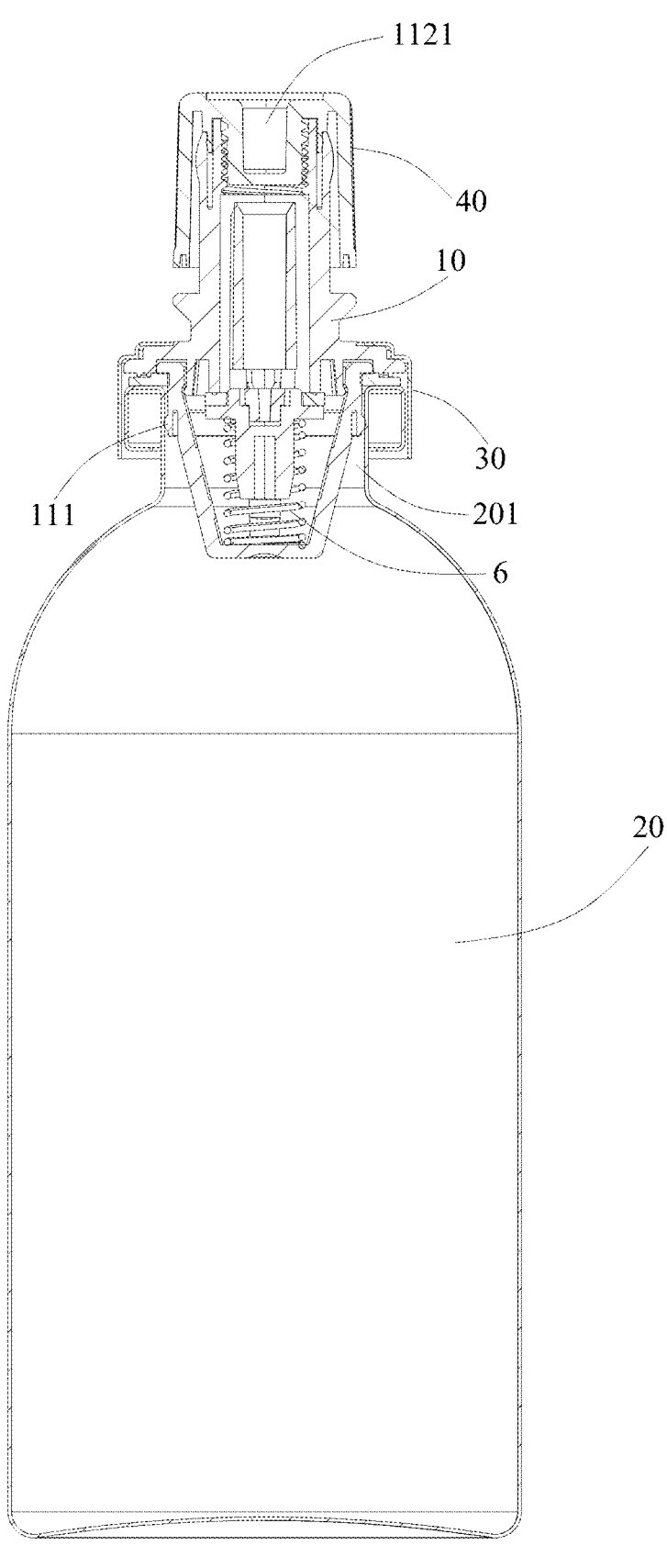
FIG. 4 is a schematic structural diagram of a closed anesthetic bottle comprising the sealing valve in FIG. 2 provided by an embodiment of the present application.

Some embodiments of the present application also provide a closed anesthetic bottle, referring to FIGS. 3 and 4. The closed anesthetic bottle includes a bottle body 20 and a sealing valve 10 as in the above-mentioned embodiment. The convex ring 111 abuts against the inner wall of the opening 201 of the bottle body 20. In a specific implementation, the bottle body 20 includes an aluminum case and an inert liner lining the inner wall of the aluminum case. The aluminum case is strong, reliable and low-cost. However, due to the chemical reaction between aluminum oxide and the drug, even if the aluminum case does not react with the drug, there may be aluminum particles or flakes inside the container due to external forces or the microscopic defects of the aluminum case itself during the manufacturing, storage and transportation of the aluminum case. The drug feeding tube of the anesthesia vaporizer may be damaged or blocked due to long-term contact with these aluminum particles or flakes, and because these aluminum particles or flakes exist in the liquid drug, the patient or his family members mistakenly believe that the drug has quality problems. Therefore, the closed anesthetic bottle provided in this embodiment is provided with an inert liner made of inert materials on the inner wall of the aluminum case; as a preferred solution of this embodiment, the materials used by inert liner include, but are not limited to: lacquer, enamel, epoxy phenolic resin, etc. Since the convex ring 111 abuts against the inner wall of the opening 201 of the bottle body 20, there is no liquid or gas overflow between the inner wall of the bottle body 20 and the outer wall of the first end 11, and when the sealing valve 10 is connected to the mouth of the bottle body 20, when a sealing ring is provided, the gas or liquid in the bottle body 20 can be prevented from overflowing and contacting the sealing ring, thereby ensuring the purity of the liquid drug in the bottle body 20 and improving the sealing property of the outer packaging bottle. At the same time, when the gas in the bottle body 20 enters the inner side of the convex ring 111, the convex ring 111 will be expanded, and the sealing property of the connection between the convex ring 111 and the inner wall of the mouth of the bottle body 20 is further improved.

In some embodiments of the present application, referring to FIGS. 1 and 2, one end of the guiding tube 1 close to the first end 11 is provided with a first connecting portion 14 in a ring shape, and the first connecting portion 14 is located outside the bottle body 20 and fixed at the opening 201 of the bottle body 20. In this way, the stability of the installation of the sealing valve 10 and the bottle body 20 can be further improved.

In some embodiments of the present application, a second sealing member 9 is provided between the first connecting portion 14 and the opening 201 of the bottle body 20, and the first connecting portion 14 includes an annular convex disk 141 integrally connected to the guiding tube 1. The annular convex disk 141 protrudes radially outward along the guiding tube 1 and is arranged around the outer tube wall of the first end 11. The annular convex disk 141 is fixed at the opening 201 of the bottle body 20; the sealing convex portion 142 is provided on the side of the annular convex disk 141 facing the gasket, and the sealing convex portion 142 extends around the guiding tube 1 in the circumferential direction of the guiding tube 1 and abuts against the second sealing member 9. The guiding tube 1 is fixed to the opening 201 of the bottle body 20 by the annular convex disk 141, and is connected to the opening 201 of the bottle body 20 by the second sealing member 9 with excellent sealing property, which can effectively prevent the substance in the container from volatilizing and spreading to the outside of the container; as a preferred solution of this embodiment, a plurality of sealing convex rings 111 are arranged concentrically and equidistantly on the annular convex disk 141 to form a multi-layer seal at the connection between the sealing valve 10 and the bottle body 20, so that the sealing property is improved. In a specific implementation, the second sealing member 9 may be in the shape of a flat ring, one side of which abuts against the annular convex disk 141 through the sealing convex portion 142, and the other side abuts against the opening 201 of the bottle body 20 to further improve the sealing property between the valve 10 and the bottle body 20. As a preferred solution of this embodiment, the second sealing member 9 is made of EVA material.

In some embodiments of the present application, referring to FIGS. 3 and 4, the closed anesthetic bottle further includes a ring cap 30 which is sheathed at the first connecting portion 14 and the opening 201 of the bottle body 20. A ring cap 30 is sheathed at the first connecting portion 14 and the opening 201 of the bottle body 20 to connect and fix the bottle body 20 with the sealing valve 10, which not only is used to cover the first connecting portion 14 with a more complicated appearance structure, but also makes the appearance more beautiful and can prevent dust accumulation.

Figure 5:
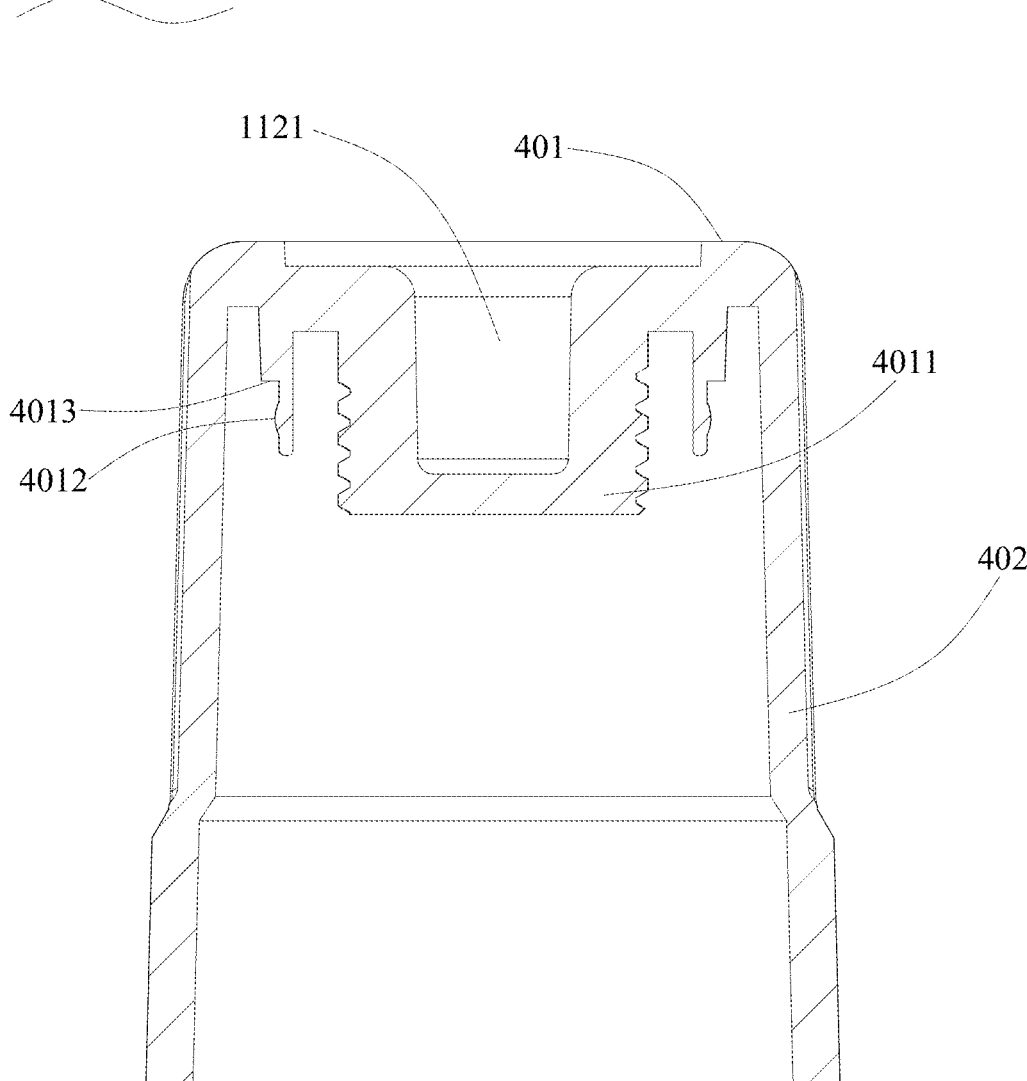
FIG. 5 is a first structural diagram of the cap of a closed anesthetic bottle provided by an embodiment of the present application.

In some embodiments of the present application, referring to FIGS. 3 to 5, the closed anesthetic bottle further includes a bottle cap 40 sleeved on the outer tube wall of the sealing valve 10, the bottle cap 40 includes a top end 401 and an open end 402, and the first end 11 of a guiding tube 1 is provided with a second connecting portion 112, and the top end 401 is provided with a third connecting portion 4011 that cooperates with the second connecting portion 112. The bottle cap 40 can be set in different colors to identify the type of liquid contained in the bottle body 20. For the sealed closed anesthetic bottle in the whole process of storage, transportation, unsealing and use, when the bottle body 20 is opaque or it is impossible to distinguish the type of liquid through the bottle body 20, the use of different colors to identify the liquid in the bottle body 20 helps the operator to distinguish and prevent the operator from taking it wrongly. In some embodiments of the present application, the closed anesthetic bottle provided in this embodiment is used to package inhaled anesthetic liquid. A yellow bottle cap 40 can be used to indicate that the liquid contained in the closed anesthetic bottle is sevoflurane. The purple bottle cap 40 indicates that the liquid contained in the closed anesthetic bottle is isoflurane, and the blue bottle cap 40 indicates that the liquid contained in the closed anesthetic bottle is desflurane. The second connecting portion 112 cooperates with the third connecting portion 4011 to install the bottle cap 40 outside of the guiding tube 1. The bottle cap 40 is used to protect the sealing valve 10, it is not only waterproof and dustproof, but also prevents foreign objects from hitting the pushing rod 2, and avoids the liquid anesthetic escaping or volatilizing during the storage and transportation. In a specific implementation, the second connecting portion 112 may be a section of the guiding tube 1 with an internal thread at the first end 11, and the third connecting portion 4011 may be an externally threaded barrel or an externally threaded rod provided on the inner side of the top end 401 and matched with the second connecting portion 112; or, the second connecting portion 112 may be a guiding tube 1 with a circular or polygonal inner tube wall of a section of the first end 11, and the third connecting portion 4011 is a cylindrical portion or rod-shaped portion provided on the inner side of the top end 401 and connected to the second connecting portion 112 in an interference-fitted way. The second connecting portion 112 and the third connecting portion 4011 are connected by a threaded or interference-fitted way, which can firmly connect and protect the sealing valve 10 and also provide a sealing effect.

In some embodiments of the present application, the top end 401 is provided with a sealing tube portion 4012, and the sealing tube portion 4012 and the third connecting portion 4011 clamp the second connecting portion 112 and hermetically cooperate with the second connecting portion 112 to further improve the sealing property of the closed anesthesia bottle. In a specific implementation, the sealing tube portion 4012 is a tubular member that is hermetically fitted with the outer tube wall of the guiding tube 1. Preferably, the inner wall of the tubular member is provided with an annular protrusion for abutting against the outer tube wall of the guiding tube 1 to ensure that the sealing tube portion 4012 is fully engaged with the guiding tube 1 to optimize the sealing property of the closed anesthetic bottle.

In some embodiments of the present application, referring to FIG. 1 and FIG. 2, the first end 11 of the guiding tube 1 is further provided with a sealing ring 113, and an annular pressure-stabilizing groove 114 is formed between the sealing ring 113 and the second connecting portion 112. The sealing tube portion 4012 is inserted into the pressure-stabilizing groove 114 and is hermetically fitted with the second connecting portion 112 and the sealing ring 113. The pressure-stabilizing groove 114 has three functions: firstly, when the drug feeding tube of the anesthesia vaporizer is inserted into the guiding tube 1, since the anesthesia vaporizer and the bottle body 20 are both sealed containers, the internal air pressure will increase gradually during the gradual insertion process, and the pressure-stabilizing groove 114 can share part of the air pressure and balance the internal pressure; secondly, with the setting of the pressure-stabilizing groove 114, inserting difficulty resulting from the internal air pressure higher than the external air pressure during the insertion process of the guiding tube 1 and the drug feeding tube of the anesthesia vaporizer will not happen, and thus it is easy to pull out, which effectively reduces the insertion and extraction force between the drug introducing structure and the anesthesia vaporizer, which is convenient for medical staff to operate; third, when a part of the air pressure fill into the pressure-stabilizing groove 114, the inner tube wall of the sealing ring 113 is compressed by air pressure and has a tendency to expand outward, which improves the tightness of the adhesion between the sealing ring 113 and the drug feeding tube of the anesthesia vaporizer, improving the sealing effect. By inserting the sealing tube portion 4012 into the pressure-stabilizing groove 114 and hermetically cooperating with the second connecting portion 112 and the sealing ring 113, the sealing property of the closed anesthetic bottle can be further optimized. In some embodiments of the present application, a limiting step 4013 is formed on the outer peripheral surface of the sealing tube portion 4012 on the side close to the top end 401. Correspondingly, the end of the second connecting portion 112 of the guiding tube 1 is higher than the end of the sealing ring 113. When the end of the second connecting portion 112 of the guiding tube 1 abuts against the top end 401, the end of the sealing ring 113 can also abut against the limiting step 4013, thereby further improving the sealing function.

In some embodiments of the present application, the open end 402 is provided with an anti-tamper ring integrally connected to the bottle cap 40, and a second annular protrusion is provided at a position corresponding to the integrated connection of the bottle cap 40 and the tamper ring on the outer tube wall of the guiding tube 1, and the inner wall of the anti-tamper ring abuts against the second annular protrusion. In a specific implementation, the bottle cap 40 and the guiding tube 1 are threadedly connected, and the anti-tamper member and the bottle cap 40 are connected by a filamentary part made from the same material as the bottle cap 40 and integrally formed with the bottle cap 40. The open end 402 of the bottle cap 40 is provided with a right-angled trapezoidal protrusion, the anti-tamper member is provided with a recess for the protrusion to be placed in. The oblique edge of the right-angled trapezoid of the protrusion corresponds to the correct direction of screwing and opening the bottle cap 40, which is used to abut against the recess during screwing and opening the bottle cap 40, which is convenient for the operator to open the bottle cap 40. The open end 402 is provided with an anti-tamper ring, and the bottle cap 40 cannot be removed from the guiding tube 1 without damaging the anti-tamper ring, so as to avoid unstable connection between the bottle cap 40 and the guiding tube 1 due to vibration during transportation.

In some embodiments of the present application, referring to FIG. 3 and FIG. 4, the second connecting portion 112 is formed by protruding inward from the outer surface of the top end 401. A side of the second connecting portion 112 close to the outer surface of the top end 401 is provided with an slot 1121, which can reduce the overall weight of the bottle cap 40 and reduce the material used, which is beneficial to its production and cost reduction.

Figure 6:
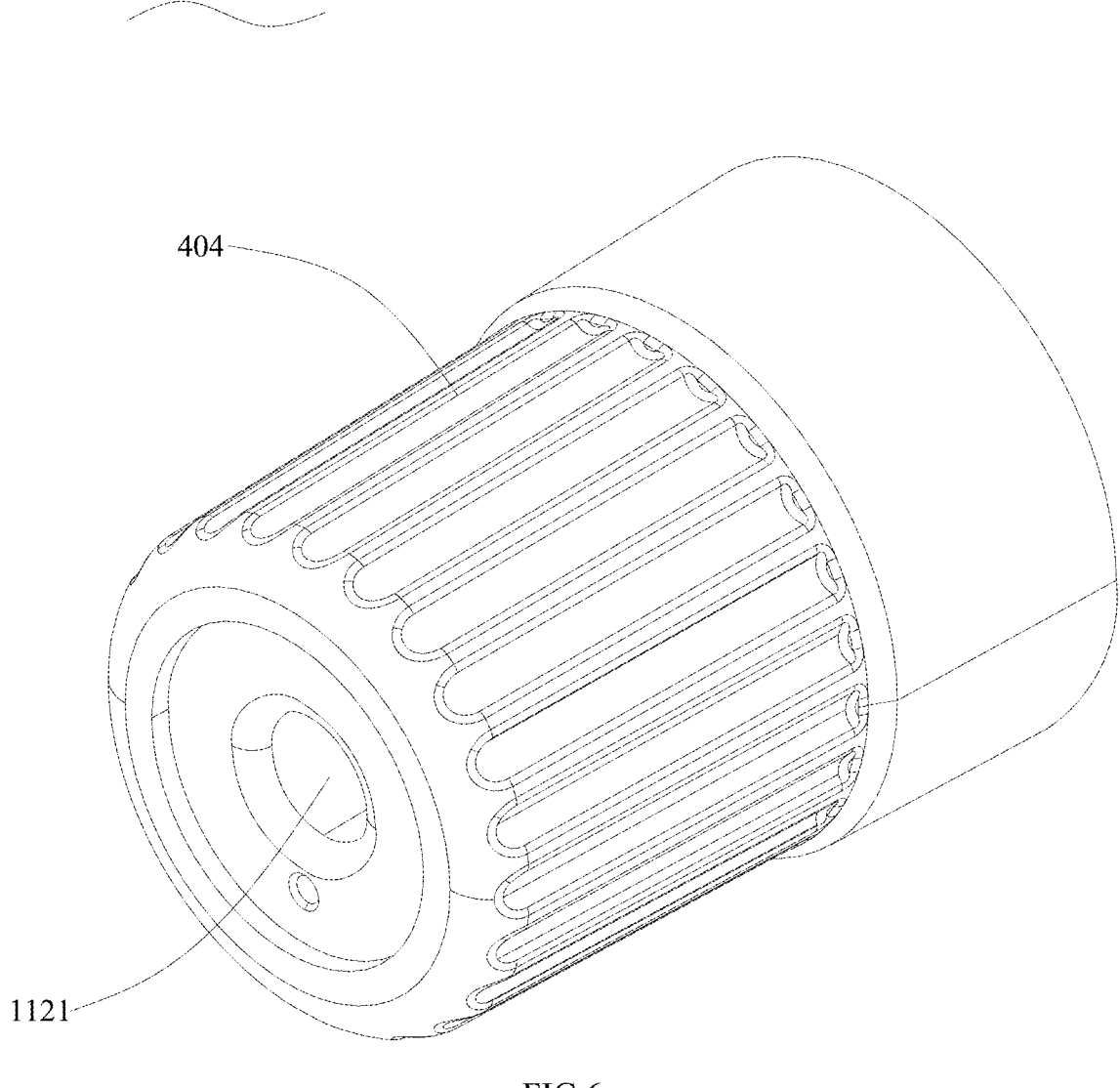
FIG. 6 is a second structural diagram of the cap of the closed anesthetic bottle provided by the embodiment of the present application.

In some embodiments of the present application, referring to FIG. 6, the outer circumference of the ring wall of the bottle cap 40 is provided with a plurality of ridges 404 to form the uneven outer peripheral surface of the bottle cap 40, which can increase the grasping force when the bottle cap 40 is unscrewed.

The above are only optional embodiments of the application, and are not used to limit the application. For those skilled in the art, this application can have various modifications and changes. Any modification, equivalent replacement, improvement, etc. made within the spirit and principle of this application shall be included in the scope of the claims of this application.

What is claimed is:

1. A sealing valve, comprising:
   a guiding tube, configured for guiding an anesthetic from an outer packaging bottle to an anesthesia vaporizer, and comprising a first end configured to be inserted into the outer packaging bottle and a second end configured to be connected to the anesthesia vaporizer;
   a convex ring, provided at an outer peripheral surface of the first end, protruding toward an inner wall of the outer packaging bottle, and abutting against the inner wall of the outer packaging bottle; and
   a pushing rod, arranged in the guiding tube and slidable along an axial direction of the guiding tube to enable the guiding tube to connect the anesthesia vaporizer with the outer packaging bottle or to block between the anesthesia vaporizer and the outer packaging bottle;
   wherein when gas inside the outer packaging bottle passes through the first end and enters an inner side of the convex ring, the gas expands the convex ring in a direction toward the inner wall of the outer packaging bottle.

2. The sealing valve of claim 1, wherein the inner tube wall of the guiding tube is provided with an annular protrusion arranged around an axis of the guiding tube, and one end of the pushing rod close to the second end abuts against the annular protrusion.

3. The sealing valve of claim 2, wherein the sealing valve further comprises a first spring and a clamping block arranged in the guiding tube, the clamping block is fixed in one end of the guiding tube close to the first end, one end of the pushing rod close to the second end is provided with a flange, the first spring is sleeved outside of the pushing rod, and both ends of the first spring abut against the flange and the clamping block, respectively.

4. The sealing valve of claim 1, wherein the sealing valve further comprises a blocking member for blocking the first end of the guiding tube and capable of moving and opening the first end of the guiding tube under the pushing of the pushing rod.

5. The sealing valve of claim 4, wherein a surface of the blocking member facing the pushing rod is provided with a positioning groove, configured for positioning the pushing rod when the pushing rod pushes the blocking member.

6. The sealing valve of claim 4, wherein the sealing valve further comprises a spring arranged in the guiding tube, configured for driving the blocking member to move to the first end to block the first end.

7. The sealing valve of claim 5, wherein the sealing valve further comprises a bracket fixed to the guiding tube, the bracket is configured to be arranged in the outer packaging bottle, the bracket is fixed to the first end and has an opening cavity and a perfusion port communicating with the opening cavity; the blocking member and a spring are both located in the opening cavity; and both ends of the spring abut against the blocking member and the bracket.

8. The sealing valve of claim 4, wherein the sealing valve further comprises a first sealing member located between the blocking member and the first end and sealing a gap therebetween.

9. The sealing valve of claim 2, wherein one end of the pushing rod close to the second end is provided with a positioning structure, configured for positioning the anesthesia vaporizer for docking when the anesthesia vaporizer is inserted into the guiding tube.

10. The sealing valve of claim 1, wherein the convex ring is a plastic convex ring, and the plastic convex ring and the guiding tube are integrally formed.

11. A closed anesthetic bottle, comprising a bottle body and the sealing valve of claim 1, wherein the convex ring abuts against the inner wall of an opening of the bottle body.

12. The closed anesthetic bottle of claim 11, wherein one end of the guiding tube close to the first end is provided with a first connecting portion in a ring shape, and the first connecting portion is located outside of the bottle body and fixed at the opening of the bottle body.

13. The closed anesthetic bottle of claim 12, wherein a sealing gasket is provided between the first connecting portion and the opening of the bottle body, the first connecting portion comprises:

an annular convex disc integrally connected to the guiding tube, the annular convex disc protrudes radially outward along the guiding tube and is arranged around an outer tube wall of the first end, and is fixed at the opening of the bottle body;

a sealing convex portion provided on a side of the annular convex disk facing the sealing gasket, the sealing convex portion surrounds the guiding tube and extends in a circumferential direction of the guiding tube and abuts against the sealing gasket.

14. The closed anesthetic bottle of claim 13, wherein the closed anesthetic bottle further comprises a ring cap sleeved on the first connecting portion and the opening of the bottle body.

15. The closed anesthesia bottle of claim 11, wherein the closed anesthesia bottle further comprises a bottle cap sleeved on an outer tube wall of the sealing valve, and the bottle cap comprises a top end and an open end, the second end of the guiding tube is provided with a second connecting portion, and the top end is provided with a third connecting portion that cooperates with the second connecting portion.

16. The closed anesthetic bottle of claim 15, wherein the top end is provided with a sealing tube portion, and the sealing tube portion and the third connecting portion clamp the second connecting portion and are hermetically fitted with the second connecting portion.

17. The closed anesthetic bottle of claim 16, wherein the first end of the guiding tube is further provided with a sealing ring, and an annular pressure-stabilizing groove is formed between the sealing ring and the second connecting portion, the sealing tube portion is inserted into the pressure-stabilizing groove and is hermetically fitted with the second connecting portion and the sealing ring.

18. The closed anesthetic bottle of claim 15, wherein the second connecting portion is formed by protruding the outer surface of the top end inward.

19. The closed anesthetic bottle of claim 18, wherein the second connecting portion is provided with an a slot on a side close to the outer surface of the top end.

20. The closed anesthetic bottle of claim 15, wherein an outer circumference of a ring wall of the bottle cap is provided with a plurality of ridges.

*     *     *     *     *